United States Patent
Mello et al.

(10) Patent No.: US 7,033,769 B2
(45) Date of Patent: Apr. 25, 2006

(54) METHOD FOR DISCOVERING ONE OR MORE PEPTIDES ADAPTED FOR SPECIFIC BINDING TO A MICROORGANISM OF INTEREST

(75) Inventors: Charlene M. Mello, Rochester, MA (US); Steven Michael Arcidiacono, Bellingham, MA (US); Jason William Soares, Framingham, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/153,524

(22) Filed: May 23, 2002

(65) Prior Publication Data

US 2004/0224358 A1 Nov. 11, 2004

(51) Int. Cl.
*G01N 33/53* (2006.01)

(52) U.S. Cl. .............................. 435/7.1; 435/6; 435/5; 435/4; 435/DIG. 17; 435/DIG. 15; 435/DIG. 14

(58) Field of Classification Search ................ 435/7.1, 435/6, 5, 4, DIG. 17, DIG. 15, DIG. 14
See application file for complete search history.

(56) References Cited

U.S. PATENT DOCUMENTS

| | | | |
|---|---|---|---|
| 4,683,202 A | | 7/1987 | Mullis |
| 5,223,408 A | | 6/1993 | Goeddel et al. |
| 5,447,914 A | | 9/1995 | Travis et al. |
| 5,631,228 A | | 5/1997 | Oppenheim et al. |
| 5,645,996 A | * | 7/1997 | Blondelle et al. ............ 435/7.1 |
| 5,646,119 A | | 7/1997 | Oppenheim et al. |
| 5,659,123 A | | 8/1997 | Van Rie et al. |
| 5,750,357 A | | 5/1998 | Olstein et al. |
| 5,798,336 A | | 8/1998 | Travis et al. |
| 5,885,965 A | | 3/1999 | Oppenheim et al. |
| 5,889,148 A | | 3/1999 | Lee et al. |
| 5,912,230 A | | 6/1999 | Oppenheim et al. |
| 5,932,701 A | | 8/1999 | Black et al. |
| 6,017,728 A | | 1/2000 | Black et al. |
| 6,143,498 A | * | 11/2000 | Olsen et al. .................. 435/6 |
| 6,159,719 A | | 12/2000 | Laine et al. |
| 6,191,254 B1 | * | 2/2001 | Falla et al. ................. 530/300 |
| 6,287,804 B1 | | 9/2001 | Black |
| 6,287,807 B1 | | 9/2001 | Wallis |
| 6,303,771 B1 | | 10/2001 | Biswas et al. |
| 6,326,462 B1 | | 12/2001 | Debouck et al. |
| 6,331,411 B1 | | 12/2001 | Gwynn et al. |
| 6,335,424 B1 | | 1/2002 | Black et al. |
| 6,335,433 B1 | | 1/2002 | Biswas et al. |
| 6,346,397 B1 | | 2/2002 | Warren, Jr. et al. |
| 6,350,598 B1 | | 2/2002 | Wallis et al. |
| 2001/0010912 A1 | | 8/2001 | Black et al. |
| 2001/0016334 A1 | | 8/2001 | Wallis et al. |
| 2001/0020010 A1 | | 9/2001 | Biswas et al. |
| 2001/0041349 A1 | | 11/2001 | Patron et al. |
| 2002/0004580 A1 | | 1/2002 | Fueyo et al. |
| 2002/0004581 A1 | | 1/2002 | Palmer et al. |
| 2002/0025537 A1 | * | 2/2002 | Bylina et al. ................ 435/7.1 |

FOREIGN PATENT DOCUMENTS

WO    PCT/US99/00771    7/1999

OTHER PUBLICATIONS

Epand et al., 'Diversity of antimicrobial peptides and their mechanisms of action,' Biochimica et Biophysica Acta, 1462:11-28 (1999).
Ostermeier et al., 'A combinatorial approach to hybrid enzymes independent of DNA homology,' Nature Biotechnology, 17:1205-9 (1999).
Sharma et al., 'Semi-automated fluorogenic PCR assays (TagMan) for rapid detection of *Escherichia coli* O157:H7 and other Shiga toxigenic *E. coli*,' Molecular and Cellular Probes, 13:291-302 (1999).
Pyle et al., 'Sensitive Detection of *Escherichia coli* O157:H7 in Food and Water by Immunomagnetic Separation and Solid-Phase Laser Cytometry,' Applied and Environmental Microbiology, 65(5) :1996-72 (1999).
Kuchner et al., 'Directed evolution of enzyme catalysts,' TIBTECH, 15 (12) :523-30 (1997).

(Continued)

*Primary Examiner*—T. D. Wessendorf
(74) *Attorney, Agent, or Firm*—Vincent J. Ranucci

(57) ABSTRACT

A method for discovering one or more peptides adapted for specific binding to a microorganism of interest. The method comprises (i) identifying an antimicrobial peptide having antimicrobial activity against the microorganism of interest, (ii) generating a library of first generation mutants of the antimicrobial peptide, each of the first generation mutants differing from the antimicrobial peptide by a small number of amino acid substitutions, additions or deletions, (iii) screening the library of first generation mutants for those first generation mutants that bind to the microorganism of interest, (iv) determining the peptide sequences of those first generation mutants that bind to the microorganism of interest, and (v) if necessary, repeating steps (ii) through (iv) for one or more successive generations of mutants until one or more consensus peptide sequences emerge.

11 Claims, 5 Drawing Sheets

OTHER PUBLICATIONS

Moore et al., 'Directed evolution of a para-nitrobenzyl esterase for aqueous-organic solvents,' Nature Biotechnology, 14:458-67 (1996).

Nicolas et al., 'Peptides as Weapons Against Microorganisms in the Chemical Defense System of Vertebrates,' Annu. Rev. Microbiol., 49:277-304 (1995).

Stemmer, 'Rapid evolution of a protein in vitro by DNA shuffling,' Nature, 370:389-91 (1994).

Lehtovaara et al., 'A new method for random mutagenesis of complete genes: enzymatic generation of mutant libraries in vitro,' Protein Engineering, 2(1) :63-8 (1998).

* cited by examiner

METHOD FOR DISCOVERING ONE OR MORE PEPTIDES ADAPTED FOR SPECIFIC BINDING TO A MICROORGANISM OF INTEREST

STATEMENT OF FEDERALLY SPONSORED RESEARCH OR DEVELOPMENT

The invention described herein may be manufactured and used by the U.S. Government for Governmental purposes without the payment of any royalty thereon.

BACKGROUND OF THE INVENTION

The present invention relates generally to the detection of microorganisms using peptides adapted for specific binding thereto and relates more particularly to a method for discovering such peptides.

Microorganisms, such as bacteria, viruses, fungi and protozoa, are commonplace in the environment. Although many such microorganisms are innocuous to humans, certain species of microorganisms are pathogenic and pose a serious health risk to people. Exposure to such pathogenic microorganisms may be inadvertent, such as in the case of poorly handled or poorly prepared foods containing *Salmonella, E. coli* O157:H7 or the like, or may be deliberate, such as in the case of biological weapons armed with spores of anthrax or the like. As can readily be appreciated, in view of the above, it is highly desirable to be able to detect the presence of pathogenic microorganisms in various media, such as food, water and air, that are likely to come into human contact. Unfortunately, the presence of pathogenic microorganisms in such media cannot typically be ascertained simply by visual or other sensory examination of the media, but rather, requires the use of specialized testing equipment and procedures. Moreover, because certain pathogenic microorganisms may be lethal in very small doses (for example, in some instances, in doses constituting as few as about ten microorganisms), comparatively large quantities of materials must often be tested for the presence of comparatively small quantities of pathogens.

One technique that is commonly used to detect the presence of a pathogenic microorganism in a sample is an enzyme linked immunosorbent assay (ELISA), such a technique employing, among other things, an antibody adapted to bind to the pathogen of interest. Examples of ELISA techniques used in the detection of pathogenic microorganisms may be found in the following U.S. patents: U.S. Pat. No.6,174,667, inventors Huchzermeier et al., which issued Jan. 16, 2001; U.S. Pat. No. 6,124,105, inventors Verschoor et al., which issued Sep. 26, 2000; U.S. Pat. No. 5,294,537, inventor Batt, which issued Mar. 15, 1994; and U.S. Pat. No. 4,486,530, inventors David et al., which issued Dec. 4, 1984.

Unfortunately, some difficulties that are commonly encountered in using ELISA technology to detect pathogens include the lack of long-term stability and/or insufficient specificity to bind only to the pathogenic microorganism of interest. Consequently, certain non-pathogenic microorganisms often become bound to such antibodies, thereby leading to the undesirable occurrence of false positive results.

Another technique that is commonly used to detect the presence of a pathogenic microorganism in a sample is a DNA-based approach that involves detecting within the sample the presence of one or more genes indicative of the pathogenic microorganism of interest. Such a DNA-based approach typically comprises inoculating a culture broth with a sample under investigation, allowing the broth to culture for a period of time (e.g., typically overnight up to a few days), isolating any microorganisms present in the broth, retrieving the DNA from the isolated microorganisms, amplifying the retrieved DNA, and using one or more hybridizing probes specific for a gene or genes of interest to detect the presence of said gene(s) within the amplified DNA. Although the aforementioned DNA-based approach does not typically suffer from the shortcoming of false positive results that are encountered in the above-described ELISA technique, it can readily be appreciated that the aforementioned DNA-based approach can be rather time-consuming, especially where there is a large quantity of sample to be tested.

Examples of other techniques for detecting the presence of a pathogenic microorganism in a sample are disclosed in U.S. Pat. No. 6,159,719, inventors Laine et al., which issued Dec. 12, 2000; U.S. Pat. No. 5,750,357, inventors Olstein et al., which issued May 12, 1998; Pyle et al., "Sensitive Detection of *Escherichia coli* O157:H7 in Food and Water by Immunomagnetic Separation and Solid-Phase Laser Cytometry," *Appl. Environ. Microbiol.*, 65(5): 1966–72 (May 1999) and Sharma et al., "Semi-automated fluorogenic PCR assays (TaqMan) for rapid detection of *Escherichia coli* O157:H7 and other Shiga toxigenic *E. coli,*" *Molecular and Cellular Probes*, 13:291–302 (1999). Unfortunately, many of the techniques described in the aforementioned publications suffer from one or more of the types of shortcomings described above.

In PCT Application No. PCT/US99/00771, inventor Tumbough, which was published Jul. 22, 1999, there is disclosed a technique for identifying peptides from a combinatorial library that bind specifically to bacterial spores of interest and that, therefore, can be used as capture probes or the like for use in detecting the presence of said spores in a sample. According to the aforementioned PCT application, said technique comprises mixing a quantity of a pathogenic spore with a commercially available (New England Biolabs) phage display library, said phage display library comprising a combinatorial library of random amino acid sequences (7-mer or 12-mer) fused to the minor coat protein (pIII) of the filamentous coliphage M13. After incubating for a sufficient period of time to allow the phage to complex with the pathogenic spores, the mixture is centrifuged to permit the isolation of the phage-spore complexes. The phage-spore complexes are washed repeatedly and the phage is then eluted from the phage-spore complexes with an elution buffer. The eluate is neutralized to prevent phage killing, and the eluted phage is then amplified by infecting *E. coli*. The cell lysate obtained from the culture is then subjected to the above series of steps repeatedly until about 3 to 4 rounds of biopanning take place. Next, individual clones are purified from the eluted phage, and phage plaques are amplified. The phage DNA is then extracted from each preparation to permit the DNA sequence that encodes the peptide to be determined.

One limitation to the above-described combinatorial phage display approach is that the peptide sequences being screened must be relatively short (i.e., in the range of 7 to 12 amino acid residues) to keep the number of members of the combinatorial library to a manageable size while, at the same time, assuring representation of all possible sequences within the library. Because of their comparatively short length, however, most of these peptides do not possess a stable secondary structure, thereby making binding specificity even more difficult.

Another limitation to the above-described combinatorial phage display approach is that it is restricted to identifying peptides from a combinatorial library that bind specifically to bacterial spores, as opposed to vegetative cells. As can readily be appreciated, because not all microorganisms form spores, an approach that is limited to spores excludes many microorganisms of interest. Moreover, as compared to spores, vegetative cells are actually active, there is clearly a considerable need to be able to detect vegetative cells as well as spores.

SUMMARY OF THE INVENTION

It is an object of the present invention to provide a novel method for discovering one or more peptides adapted for binding, with a high degree of specificity and/or affinity, to a microorganism of interest.

The present invention is based on the unexpected discovery that one or more peptides that possess a high degree of binding specificity and/or affinity for a microorganism of interest can be discovered by (i) identifying an antimicrobial peptide having antimicrobial activity against and/or binding affinity to the microorganism of interest, (ii) generating a library of first generation mutants of said antimicrobial peptide, each of said first generation mutants differing from said antimicrobial peptide by a number of amino acid substitutions, additions, or deletions, (iii) screening said library of first generation mutants for those first generation mutants that bind to said microorganism of interest, (iv) determining the peptide sequences of those first generation mutants that bind to said microorganism of interest, and (v) if necessary, repeating steps (ii) through (iv) for one or more successive generations of mutants until one or more consensus peptide sequences emerge.

According to a first embodiment of the invention, each library of mutants is created by a method comprising the steps of (i) providing an oligonucleotide sequence that encodes the aforementioned antimicrobial peptide, (ii) creating a library of mutant oligonucleotide sequences by random mutagenesis so as to encode approximately 1–2 amino acid substitutions, additions or deletions per peptide, (iii) incorporating each mutant oligonucleotide sequence into a suitable vector of a peptide display system (which may be, for example, a yeast, *E. Coli* or phage display system), and (iv) expressing the peptide corresponding to the mutant oligonucleotide as part of a fusion protein with a cell-surface protein of said peptide display system. Said library of mutants is then screened by (i) incubating the cell-surface displayed peptides with a quantity of the microorganism of interest for a sufficient period of time to allow binding between the peptide and the microorganism, (ii) isolating displayed peptide/microorganism complexes by centrifugation of the mixture, (iii) washing the complexes under increasing conditions of stringency, (iv) eluting the cell-surface displayed peptides from the complexes, and (v) amplifying the eluted cell-surface displayed peptides. The DNA sequences encoding the peptides from the isolated complexes are then determined, and, if necessary, the foregoing steps are repeated until one or more consensus peptide sequences are identified.

According to a second embodiment of the invention, the antimicrobial peptide is first analyzed to determine which amino acid residues therein are most important to binding affinity. A library of first generation mutants is then synthesized wherein those residues in the antimicrobial peptide previously found to be important to binding affinity are conserved and a number of other residues (typically neighboring residues) are substituted in a combinatorial fashion. In accordance with this second embodiment, the screening of peptides for binding affinity may be performed by labeling the synthesized peptides with a fluorescent tag, immobilizing the microorganism of interest within the wells of a microtiter plate, adding the labeled peptides to the wells, allowing the labeled peptides to bind to the microorganism, washing the wells to remove unbound peptides, observing which wells exhibit fluorescence attributable to the bound peptide, identifying the sequences of the bound peptides and, if necessary, synthesizing and screening one or more successive generation mutant libraries until one or more consensus sequences are identified. Alternatively, the screening peptides for binding affinity may be performed by immobilizing the synthesized peptides within the wells of a microtiter plate, adding the microorganism of interest to the wells, allowing the microorganism to bind the immobilized peptide, adding to the wells an enzyme-linked antibody against the microorganism, adding a substrate to the wells that exhibits a color change catalyzed by said enzyme and then detecting a color change.

As can readily be appreciated, the foregoing techniques can be applied to fragments of an antimicrobial peptide, as well as to the full-length antimicrobial peptide.

The present invention is also directed to those peptides identified in accordance with the present method and to the use of such peptides in biosensors for detecting the presence of pathogenic and other microorganisms of interest and/or in filters or other separation, sample preparation or detection devices for removing and/or identifying such microorganisms from various media.

Additional objects, as well as features and advantages, of the present invention will be set forth in part in the description which follows, and in part will be obvious from the description or may be learned by practice of the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1A:
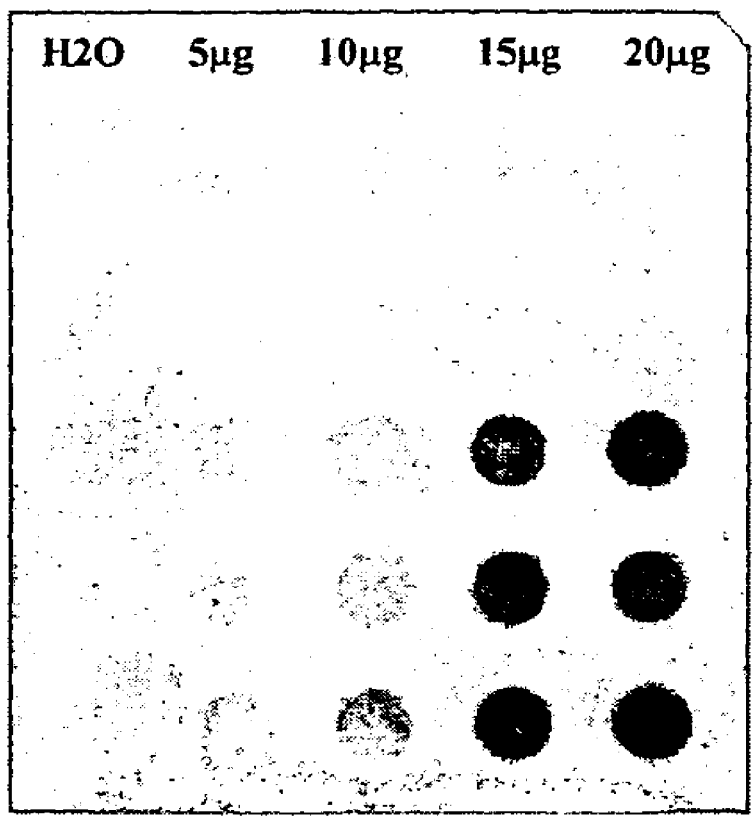
FIGS. 1(*a*) and 1(*b*) are images of the dot blot results obtained in Example II for the binding of various antimicrobial peptides to *E.coli* and *Salmonella*, respectively.

As noted above, the present invention is based on the unexpected discovery that an antimicrobial peptide having antimicrobial activity and/or binding affinity against a microorganism of interest can be used to discover mutant peptides that bind, with a comparatively high degree of specificity and/or affinity, to said microorganism of interest.

Antimicrobial peptides, i.e., naturally-occurring peptides having antimicrobial activity, have received increasing attention over the last several years as a possible means of treating microbial infections. See e.g., U.S. Pat. No. 6,042,848, inventors Lawyer et al., which issued Mar. 28, 2000; U.S. Pat. No. 5,914,248, inventors Kuipers et al., which issued Jun. 22, 1999; U.S. Pat. No. 5,912,230, inventors Oppenheim et al., which issued Jun. 15, 1999; U.S. Pat. No. 5,889,148, inventors Lee et al., which issued Mar. 30, 1999; U.S. Pat. No. 5,885,965, inventors Oppenheim et al., which issued Mar. 23, 1999; U.S. Pat. No. 5,861,275, inventor Hansen, which issued Jan. 19, 1999; U.S. Pat. No. 5,856,127, inventors Powell et al., which issued Jan. 5, 1999; U.S. Pat. No. 5,844,072, inventors Selsted et al., which issued December 1, 1998; U.S. Pat. No. 5,798,336, inventors Travis et al., which issued Aug. 25, 1998; U.S. Pat. No. 5,646,119, inventors Oppenheim et al., which issued Jul. 8, 1997; U.S. Pat. No. 5,631,228, inventors Oppenheim et al., which issued May 20, 1997; U.S. Pat. No. 5,519,115, inventors Mapelli et al., issued May 21, 1996; U.S. Pat. No. 5,447,914, inventors Travis et al., which issued Sep. 5, 1995; Epand et al., "Diversity of antimicrobial peptides and their mechanisms of action, "Biochimica et Biophysica Acta, 1462: 11–28 (1999); and Nicolas et al., "Peptides as Weapons Against Microorganisms in the Chemical Defense System of Vertebrates," Annu. Rev. Microbiol., 49:277–304 (1995).

Most antimicrobial peptides are not limited in activity to a specific microorganism, but rather, typically have antimicrobial activity against a rather wide range of microbes. The actual mechanism by which antimicrobial peptides function is not, at present, particularly well-understood; nevertheless, one of the more common modes of operation appears to be for the antimicrobial peptide to insert itself into the cell membrane of the microbe in such a way as to create pores through which the microbial cytoplasm empties, thereby killing the microbe. It should be noted however, that scant, if any, attention in the literature has heretofore been paid to any binding occurring between the antimicrobial peptide and the microbial cell membrane as a prelude to the above-described insertion of the antimicrobial peptide into the microbial cell membrane. In fact, many antimicrobial peptides bind rather poorly to the microbes against which they exhibit antimicrobial activity.

Notwithstanding the above, the technique of the present invention exploits the fact that some degree of binding does occur between the antimicrobial peptide and the microbe. Therefore, antimicrobial peptides are used as templates from which libraries of mutants can be generated and screened to identify selected mutants having heightened specificity or binding affinity for a microbe of interest. More specifically, the method of the present invention comprises the following steps: (i) identifying an antimicrobial peptide having antimicrobial activity or binding affinity for a microorganism of interest, (ii) generating a library of first generation mutants of said antimicrobial peptide, each of said first generation mutants differing from said antimicrobial peptide by a number of amino acid substitutions, additions or deletions, (iii) screening said library of first generation mutants for those first generation mutants that bind to said microorganism of interest, (iv) determining the peptide sequences of those first generation mutants that bind to said microorganism of interest, and (v) if necessary, repeating steps (ii) through (iv) for one or more successive generations of mutants until one or more consensus peptide sequences emerge.

As noted above, the first step of the present method involves identifying a suitable antimicrobial peptide that can be used as a template to discover binding-specific mutants. Suitable antimicrobial peptides are those exhibiting antimicrobial affinity or whole-cell binding affinity against the microorganism of interest and may be found from a review of the scientific literature and/or by screening candidate antimicrobial peptides. In addition, for reasons to become apparent below, suitable antimicrobial peptides for purposes of the present invention preferably have a length of about 7–50 amino acids, more preferably about 30–50 amino acids, and preferably do not have any post-translational modifications.

Where a large number of suitable antimicrobial peptides against the microorganism of interest have been identified, it may be preferable to select from said group a smaller number of antimicrobial peptides (preferably about 1–4 antimicrobial peptides) exhibiting comparatively greater binding affinity for the particular microorganism. The screening of a large number of antimicrobial peptides for such a small number having high binding affinity may be performed using a dot blot technique or the like. The selected small number of antimicrobial peptides preferably exhibit sequence diversity from one another to avoid redundancy and possibly to permit the identification of mutants capable of binding to different portions of the microorganism of interest.

Once the small number of antimicrobial peptides for use in the present method have been identified, a plurality of techniques exist for generating mutants thereof and for screening said mutants until consensus sequences of specific binding to the microorganism emerge.

According to a first embodiment of the invention, the generation of said mutants of each antimicrobial peptide may be performed as follows: First, an oligonucleotide sequence that encodes each such antimicrobial peptide is prepared. Next, said one or more oligonucleotide sequences are cloned into peptide display vectors (such as yeast, E.coli or phage display vectors), and the expression of said one or more oligonucleotide sequences as antimicrobial peptides fused to a cell-surface protein is demonstrated. Next, the binding of said one or more antimicrobial peptide fusion proteins to the microorganism of interest is demonstrated. Then, for each such antimicrobial peptide, a library of mutant oligonucleotide sequences is generated by random mutagenesis so as to encode approximately 1–2 amino acid substitutions, additions or deletions per antimicrobial peptide. Examples of suitable random mutagenesis techniques for purposes of the present invention include, but are not limited to, error-prone polymerase chain reaction (see U.S. Pat. No. 5,223,408, inventors Goeddel et al. and degenerate oligonucleotide mutagenesis (see Lehtovaara et al., "A new method for random mutagenesis of complete genes: enzymatic generation of mutant libraries in vitro, "Protein Engineering, 2(1):63–8 (1998)). Next, each mutant oligonucleotide sequence is incorporated into a peptide display vector, and the peptides corresponding to the mutant oligonucleotide sequences are expressed as fusion proteins with a cell-surface protein (e.g., a phage coat protein in the case of a phage display system).

A library of mutants thus generated may then screened by (i) incubating the peptide-displayed (e.g., phage-displayed) peptides with a quantity of the microorganism of interest for a sufficient period of time to allow binding between the peptide and the microorganism, (ii) isolating peptide/microorganism complexes by centrifugation of the mixture, (iii) washing the complexes under increasing conditions of stringency, (iv) eluting the displayed-peptides from the complexes, and (v) amplifying the eluted displayed-peptides. The DNA sequences encoding the peptides from the isolated complexes are then determined, and, if necessary, the foregoing steps are repeated until one or more consensus sequences are identified.

According to a second embodiment of the invention, once an antimicrobial peptide has been identified as suitable for purposes of the present invention, the antimicrobial peptide is then analyzed to determine which amino acid residues therein are most important to binding affinity. Such an analysis typically involves, as a first step, generating and testing partial sequences of the antimicrobial peptide to determine which region or regions of the peptide are most important to binding affinity. (For example, for an antimicrobial peptide that is 30 amino acid residues in length, five peptides corresponding to residues 1–10, 11–20, 21–30, 5–15 and 16–25, respectively, may be generated and tested for binding affinity.) Once the one or more regions of binding affinity have been determined, individual amino acid residues therewithin that affect binding affinity are then ascertained using techniques, such as scanning-alanine mutagenesis (see U.S. Pat. No. 5,223,408, inventors Goeddel et al., which issued Jun. 29, 1993; and U.S. Pat. No. 5,659,123, inventors Van Rie et al., which issued Aug. 19, 1997; Cunningham et al., Science, 244:1081–5 (1989).

Once the antimicrobial peptide has been analyzed in the manner described above, a library of first generation mutants of each antimicrobial peptide is synthesized wherein those residues therein found to be most important to binding affinity are conserved and a small number of other residues (typically neighboring residues) are substituted in a combinatorial fashion. (If desired, certain amino acids, like cysteine, may be omitted from the combinatorial array of substitutions. In addition, certain non-naturally occurring amino acids (for example, those having similar functionalities to the wild type residues but which may impart additional stability to the peptide) may be included in the combinatorial array of substitutions. Moreover, in stead of generating a library of mutants corresponding to the whole antimicrobial peptide, the mutants may be shorter peptides directed solely to said one or more regions of the antimicrobial peptide most intimately associated with binding affinity.) In accordance with this second embodiment, the screening of peptides for binding affinity is then preferably performed by labeling the peptides (e.g., by coupling biotin or another fluorescent tag to the end of the peptide via a cysteine residue added to the end of the peptide), immobilizing the microorganism of interest in the wells of a microtiter plate, adding the labeled peptides to the wells, allowing the labeled peptides to bind to the pathogen, washing the wells to remove unbound peptides, and using the label to detect which wells contain the bound peptide. The sequences of the bound peptides are then determined and, if necessary, one or more successive generation mutant libraries of the foregoing bound proteins are synthesized and screened in the above-described manner until one or more consensus sequences are identified. Alternatively, the screening of peptides for binding affinity may be performed by immobilizing the synthesized peptides within the wells of a microtiter plate, adding the microorganism of interest to the wells, allowing the microorganism to bind to the immobilized peptide, adding to the wells an enzyme-linked antibody against the microorganism, adding a substrate to the wells that exhibits a color change catalyzed by said enzyme and then detecting a color change.

The following examples are provided for illustrative purposes only and are in no way intended to limit the scope of the present invention:

EXAMPLE I

Identification of Possible Antimicrobial Peptides for use in Invention Based on Review of Literature After a review of the literature, the following nine antimicrobial peptides were identified as possible candidates for use as antimicrobial peptides in accordance with the teachings of the present invention for use in discovering mutant peptides that bind with a comparatively high degree of specificity and/or binding affinity to $E.coli$ O157:H7: (1) Buforin I (see Park et al., "A novel antimicrobial peptide from $Bufobufo$ $gargarizans$," Biochem Biophys. Res. Commun. 218:408–13 (1996)); (2) Buforin II (see Park et al. above); (3) Cecropin A (see Sun et al., "Peptide sequence of an antibiotic cecropin from the vector mosquito, *Aedes albopictus*, "Biochem. Biophys. Res. Commun. 249:410–5 (1998)); (4) SMAP-29 (see Mahoney et al., "Molecular analysis of the sheep cathelin family reveals a novel antimicrobial peptide, "FEBS Lett. 377:519–22 (1995)); (5) Cecropin P1 (see Lee et al., "Antibacterial peptides from pig intestine isolation of a mammalian cecropin, "Proc. Natl. Acad. Sci. U.S.A., 86:9159–62 (1989)); (6) Ceratotoxin A (see Marchini et al., "cDNA sequence and expression of the ceratotoxin gene encoding an antibacterial sex-specific peptide from the medfly *Ceratitis capitata* (diptera)," J. Biol. Chem., 270:6199–204 (1995); and Cole et al., "Isolation and characterization of pleurocidin, an antimicrobial peptide in the skin secretions of winter flounder," J. Biol. Chem. 272:12008–13 (1997)); (7) Caerulein (see Anastasi et al., "Presence of caerulein in extracts of the skin of Leptodacytlus pentadactylus labryinthicus and of *Xenopus laevis*," Br. J. Pharmocol., 38:221–8 (1970)); (8) PGQ (see Moore et al., "Antimicrobial peptides in the stomach of *Xenopus Laevis*," J. Biol. Chem., 266:19851–7 (1991)); and (9) Pleurocidin (see Cole et al. above).

All nine of the foregoing antimicrobial peptides were chosen based on *E.coli* antimicrobial activity (and, thus, presumed *E.coli* binding) and based on the absence therein of disulfide bonds, c-terminal amidation or any other post-translation modifications. In addition, all peptides are strongly basic and form amphipathic helical structures.

EXAMPLE II

Testing of Possible Antimicrobial Peptides for Lipopolysaccharide (LPS) Binding Affinity Buforin I, Buforin II, Cecropin P1 and PGQ were tested for binding to lipopolysaccharides preparations from *E. coli* and *Salmonella* as follows (Indolicidin, another antimicrobial peptide, was tested as well): The antimicrobial peptides, which were obtained from Sigma Chemical Co., St. Louis Mo., were diluted with distilled/deionized water and were added to a Minifold I —Dot Blot apparatus (Schleicher-Schuell, Keene, N.H.) for application to an Immobilin $P^{sq}$ PVDF membrane (Millipore, Bedford, Mass.). Varying amounts of each peptide (ranging from 0–20 μg in 5 μg increments) were absorbed at a flow rate of approximity 0.15 ml/min. The membrane was blocked with 3% gelatin in TBS for 30 minutes at room temperature with gentle agitation and then was washed three times with TBS. Isolated, flourescently-labeled lipopolysaccharides (FITC-LPS) from *E. coli* and *Salmonella* (Sigma Chemical Co.) were diluted in TBS to a final concentration of 10 µg/ml and were then bound to the membrane at room temperature with gentle agitation. The membrane was then washed three times with TBS and imaged on a Storm 860 (Molecular Dynamics, Sunnyvale, Calif.) in blue flourescence mode.

Figure 1B:
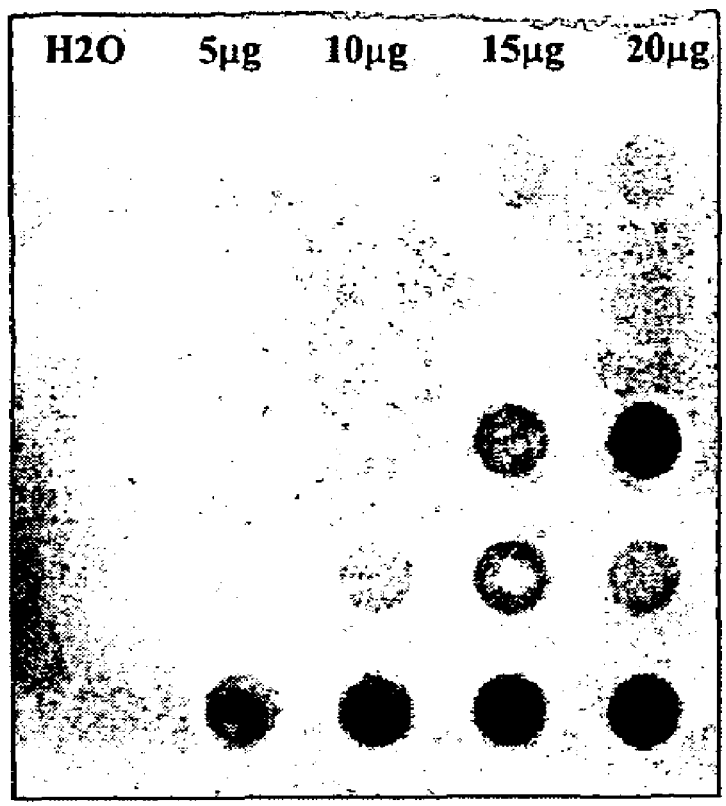

As can be seen in FIGS. 1(*a*) and 1(*b*), Buforin I and Buforin II did not bind to lipopolysaccharides from *E. coli* and *Salmonella*. Consequently, these two antimicrobial peptides may not merit further consideration as templates for use in generating mutants possessing heightened specificity and/or binding affinity. By contrast, cecropin P1, indolicidin and PGQ did bind to lipopolysaccharides from both *E.coli* and *Salmonella* and are therefore candidates identified for mutagenisis. Moreover, the binding was concentration dependent, and the strength of binding varied between the two microbial species. Such data suggests that an array of different naturally-occurring peptides may be suitable for identification and biosensor applications. More importantly, peptides developed as a result of the method disclosed herein will result in increased selectivity and binding strength relative to the native peptide, thereby improving the performance of an array-based biosensor.

EXAMPLE III

Testing of Binding of Cecropin P1 to Whole Cells

The binding of cecropin P1 to whole *E.coli* cells was tested as follows: Preparation of whole bacterial cells—*E coli* serotype O157:H7 (non-pathogenic) cells from a frozen stock were grown overnight in Luria Broth Base (Life Technologies, Inc., Paisely, Scotland). The bacterial cells were collected by centrifugation at 9000×g for 5 min. The cell pellet was washed 2 times with PBS pH 7.2 and collected each time by centrifugation. The washed cell pellet was resuspended in PBS pH 7.2 to a final volume equivalent to the original culture volume. Optical density of the cell suspension was detected on a Beckmann DU840 spectrophotometer at an absorbance of 540 nm. An absorbance of 4.5 is approximately $3.5 \times 10^9$ cfu/ml.

Peptide immobilization—Cys-Cecropin P1 (a modified cecropin p1 prepared by solid phase peptide synthesis wherein cysteine is added to the C-terminus of cecropin p1) was diluted into PBS pH 6.5, 1 mM EDTA, 0.0001 mM DTT (Sigma Chemical Co., St. Louis, Mo.) for immobilization onto sulfhydryl-bind strip wells (Corning Inc., Corning, N.Y.). A volume of 100 µl of each cys-cecropin p1 dilution was added in triplicate to the strip wells and allowed to bind to the surface for 1 hr at room temperature with gentle agitation. Strip wells were washed three times with 150 µl PBS pH 7.2 for 5 minutes per wash to remove any unbound peptide. The remaining active sites on the strip wells were blocked with 1% BSA in PBS pH 7.2 by adding 150 µl of blocking solution to each well and incubating without agitation for 30 minutes at room temperature.

Detection and color development—*E.coli* O157:H7 cells (prepared as above) were added to each well containing immobilized cys-cecropin p1 (described as above). A volume of 100 µl of each cell suspension was incubated in each well for 1.5–2 hours with gentle agitation on a rocker at room temperature. Cell suspensions were decanted and wells were washed 5 times with 150 µl PBS pH 7.2 for 5 minutes per wash to remove any unbound whole bacterial cells. An anti-*E. Coli* O157:H7 antibody conjugated with horseradish peroxidase (KPL Inc., Gaithersburg, Md.) was diluted 1:1000 with 1% BSA, PBS pH 7.2, added to each well, incubated for 1 hour at room temperature, and washed six times with 150 µl of PBS pH 7.2 for 5 minutes per wash for removal of any unbound or non-specifically bound antibody. Equal volumes of the 2-component TMB peroxidase substrate system (KPL Inc.) were prepared according to the manufacturer's protocol. The color development solution was then added to each well and allowed to incubate for 25 min. at room temperature. Absorbance was then measured on a Thermomax microplate reader (Molecular Devices, Sunnyvale, Calif.) at 650 nm.

Figure 2:
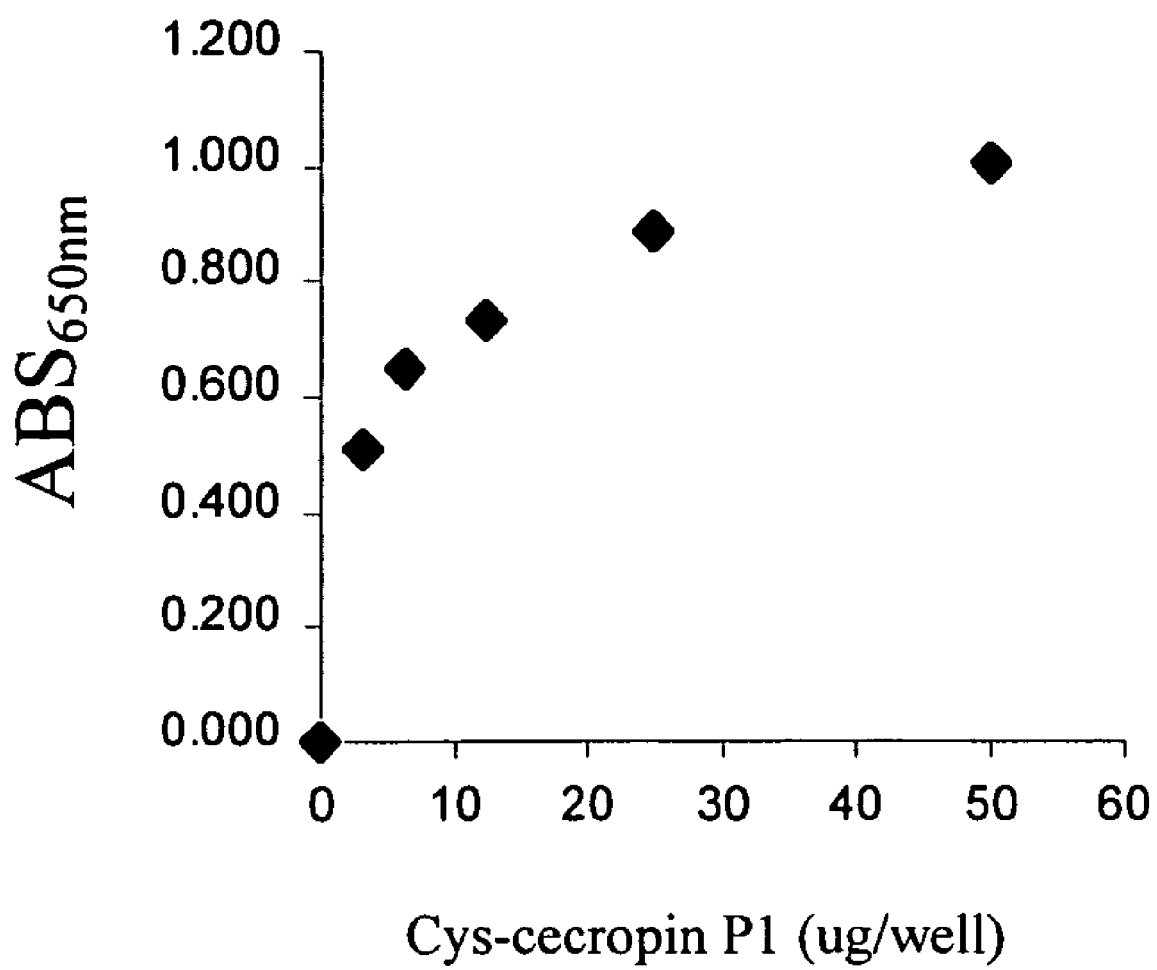
FIG. 2 is a graph depicting the concentration-dependent whole-cell binding of *E. Coli* to immobilized Cecropin P1, as described in Example III.

As can be seen in FIG. 2, immobilized cys-cecropin p1 binds to *E.coli* whole cells in a concentration-dependent manner (much in the same way that cecropin p 1 bound to the lipopolysaccharide of Example II). Saturation occurs at a concentration of 45–50 µg of cecropin p1. It is not clear if the saturation is due to the concentration of peptide immobilized or the maximum detection limit of whole cells potentially due to spatial hindrance.

EXAMPLE IV

Application of Phage Display Technique to Antimicrobial Peptide PGO

Figure 3:
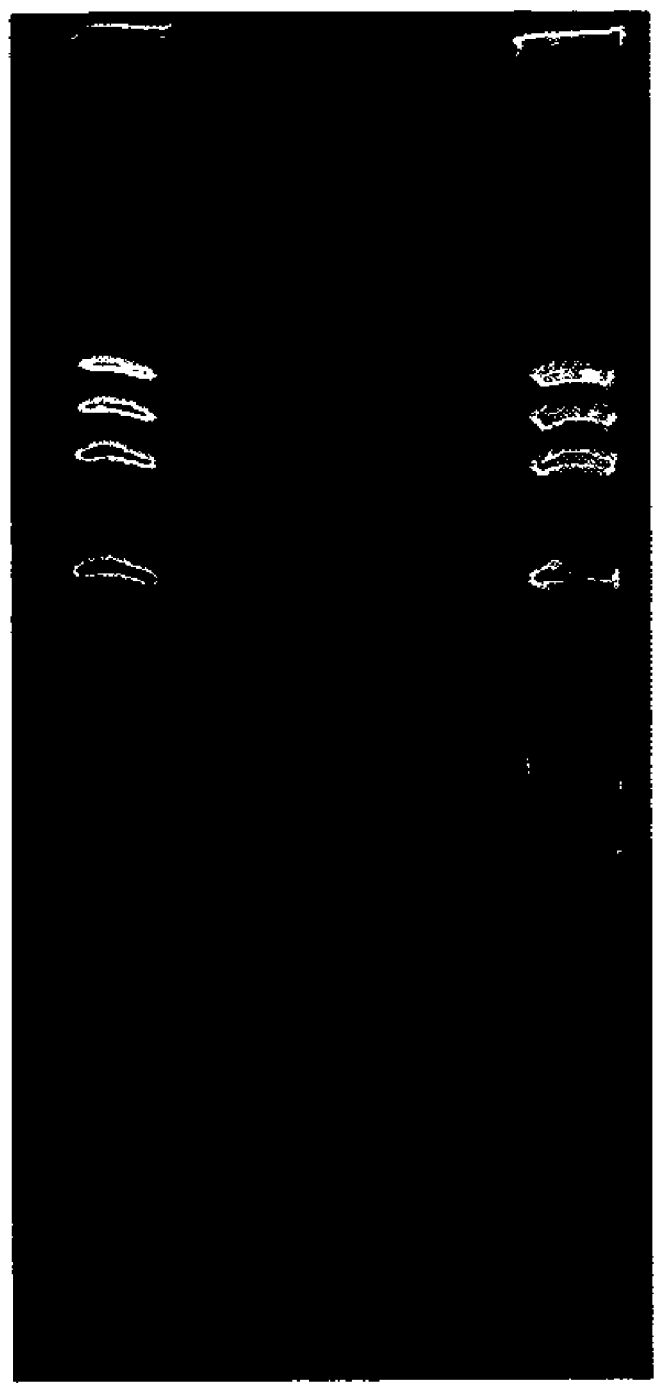
FIG. 3 is an image of a polyacrylamide gel, showing the presence of the PGQ gene in a PGQ clone.

A gene encoding the antimicrobial peptide PGQ was cloned into the T7 phage using the T7 Select Phage Display Kit (Novagen Inc., Madison, Wis.) and expressed on the phage as a fusion with the phage coat protein. The DNA encoding the coat-PGQ fusion was isolated by PCR using T7 phage primers supplied by Novagen and characterized by gel electrophoresis (see FIG. 3).

Figure 4:
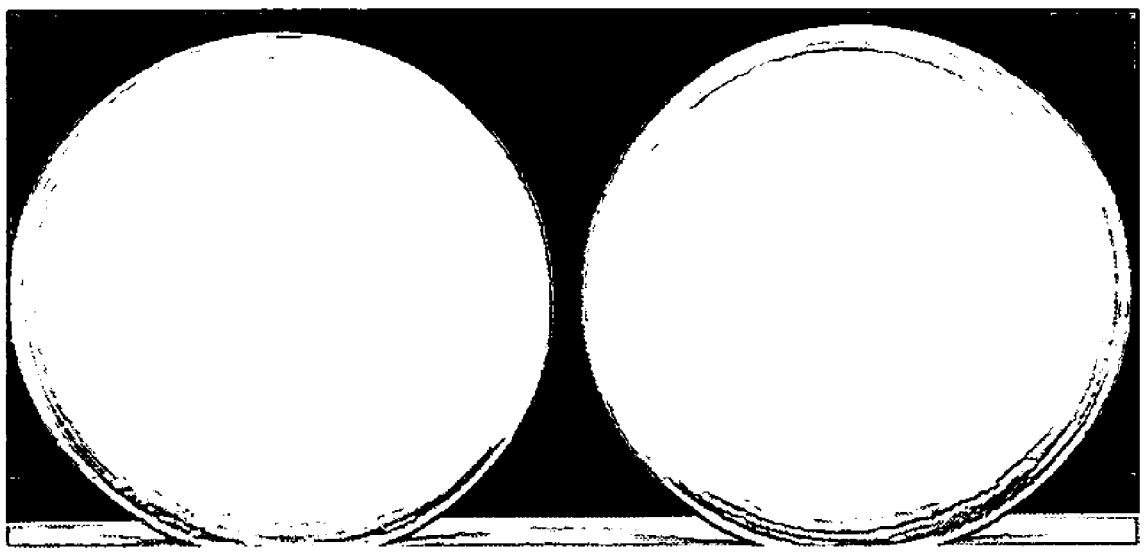
FIG. 4 is an image of a pair of plates showing the results of the cell binding assay described in Example IV.

Phage expressing the PGQ peptide were bound to *E. coli* using a method based on Liang et al., "The Hemopexin-Type Repeats of Human Vitronectin Are Recognized by *Streptococcus* pyogenes," *Biochemical and Biophysical Research Communications*, 234:445–455 (1997). The target organism, *E.coli* O157:H7, was grown to $OD_{600}=1$ in LB broth. Cells were collected by centrifugation at 10,000×g for 3 min. The supernatant was removed and the cell pellet washed 2× with an equal volume of PBS and treated as above. The pellet was resuspended in an equal volume 1×PBS/3% BSA/0.1% Tween 20 for 1 hour at ambient temperature with rocking. 200 µl phage lysate ($10^{11}$ PFU/ml) was added to 500 µl of cells and mixed at ambient temperature for 2 hours. Cells and bound phage were collected by centrifugation as above and the supernatant discarded. The pellet was washed 5× with 500 µl of PBST (PBS/0.1% Tween 20), centrifuged as above and supernatant aspirated. The phage were eluted with 200 µl of 0.3N sodium acetate, pH 5.2. Spin and collect supernatant. Tightly bound phage were collected by lysing *E. coli* O157:H7 cells in 200 µl of 0.1 M glycine-HCl, pH 2.2 and immediately neutralizing with 12 µl of 2 M Tris pH 10. 250 µl of BL21 cells ($OD_{600}$) were infected with 100 µl of sodium acetate eluted phage and glycine-HCl lysate. 3 ml of molten top agarose (per 100 ml: 1 g tryptone, 0.5 g yeast extract, 0.5 g NaCl, 0.6 g agarose) was added and the mixture applied to LB Plates (pH 7.5). The plates were incubated overnight at 37° C. for 3 hours to determine the number of plaque forming units (pfu). The results are shown in FIG. 4 and in the Table below.

TABLE

| Number PFU eluted from *E. coli* O157:H7 | | |
|---|---|---|
| Elution buffer | No insert (neg. control) | T7-PGQ |
| Sodium acetate | too many to count | too many to count |
| Glycine-HCl | 0 | 106 |

EXAMPLE V

Solid Phase Peptide Synthesis

The following peptide fragments of antimicrobial peptides were synthesized using standard FMOC solid phase chemistry for use in determining regions of the native peptides involved in whole cell binding: Cecropin A—fragments corresponding to (i) residues 1–10, (ii) residues 11–21, (iii) residues 22–35, (iv) residues 6–17, and (v) residues 18–31; Cecropin P1—fragments corresponding to (i) residues 1–10, (ii) residues 11–21, (iii) residues 22–31, (iv) residues 5–17, and (v) residues 18–27; Ceratotoxin A—fragments corresponding to (i) residues 22–29, (ii) residues 6–17, and (iii) residues 18–29; SMAP-29—fragments corresponding to (i) residues 1–8; (ii) residues 9–18; (iii) residues 19–29; (iv) residues 6–14; and (v) residues 15–23; PGQ—fragments corresponding to (i) residues 1–10; (ii) residues 11–21; (iii) residues 6–15, and (iv) residues 16–24; and Pleurocidin—fragments corresponding to (i) residues 1–12, (ii) residues 13–22, (iii) residues 6–16, and (iv) residues 17–25. Each of the aforementioned peptide fragments further included a cysteine residue at its C-terminus to permit its immobilization on a substrate. (If desired, one or more glycine residues could be inserted between the peptide fragment and the cysteine residue to give the peptide fragment a certain degree of flexibility.) Dot blot and whole cell binding assays of the type described above will be conducted, and the data obtained therein will be used to select regions of the peptide for combinatorial synthesis and selection.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for discovering at least one peptide having a specificity and/or binding affinity; to a microorganism of interest, said microorganism of interest is *E. coli*, said method comprising:
   (a) selecting an antimicrobial peptide having antimicrobial activity against and/or binding affinity to *E. coli*, said antimicrobial peptide is selected from the group consisting of cecropin A, SMAP-29, cecropin p1, ceratotoxin A, caezulein, PGQ and pleurocidin;
   (b) generating a combinatorial library of mutants of said antimicrobial peptide, each of said mutants differing from said antimicrobial peptide by amino acid substitutions, additions or deletions;
   (c) screening said library of mutants for those mutants that bind to *E. coli*;
   (d) determining the peptide sequences of those mutants that bind to *E. coli*; and
   (e) repeating steps (b) through (d) for successive generations of mutants until at least one peptide displaying heightened specificity and/or affinity obtained.

2. The method as claimed in claim 1 wherein said generating step comprises:
   (i) providing an oligonucleotide sequence that encodes said antimicrobial peptide,
   (ii) creating a library of mutant oligonucleotide sequences by random mutagenesis of said oligonucleotide sequence wherein each such mutant oligonucleotide sequence encodes approximately 1–2 amino acid substitutions, additions or deletions,
   (iii) incorporating each mutant oligonucleotide sequence into a suitable vector of a peptide display system, and
   (iv) using said suitable vector to express each mutant oligonucleotide sequence as part of a fusion protein with a cell-surface protein of said peptide display system.

3. The method as claimed in claim 2 wherein said random mutagenesis is performed using error-prone polymerase chain reaction.

4. The method as claimed in claim 2 wherein said random mutagenesis is performed using degenerate oligonucleotide mutagenesis.

5. The method as claimed in claim 2 wherein said screening step comprises:
   (i) incubating said library of mutants with a quantity of *E. coli* for a sufficient period of time to allow binding between the mutants and the microorganism in such a way as to form peptide/microorganism complexes,
   (ii) separating, by centrifugation, peptide/microorganism complexes from unbound peptides and unbound microorganism,
   (iii) washing the peptide/microorganism complexes under increasing conditions of stringency,
   (iv) eluting the peptide from the peptide/microorganism complexes, and
   (v) amplifying the eluted peptides.

6. The method as claimed in claim 5 wherein said mutants are peptides expressed on phage.

7. A method for discovering at least one peptide having binding affinity for a microorganism of interest, said microorganism of interest is *E. coli*, said method comprising:
   (a) selecting an antimicrobial peptide having antimicrobial activity against or binding affinity to *E. coli*, said antimicrobial peptide is selected from the group consisting of cecropin A, SMAP-29, cecropin p1, ceratotoxin A, caerulein, PGQ and pleurocidin;
   (b) determining which amino acid residues in said antimicrobial peptide are important to binding affinity, and replacing each native amino acid residue of said antimicrobial peptide with alanine one at a time and then testing said replacements to identify those amino acid residues important to binding affinity;
   (c) generating a combinatorial library of mutants of said antimicrobial peptide, each of said mutants differing from said antimicrobial peptide by a number of amino acid substitutions, additions or deletions; and conserving those amino acid residues found to be important to binding affinity and substituting other selected amino acid residues;
   (d) screening said library of mutants for those mutants that bind to *E. coli*; and
   (d) determining the peptide sequences of those mutants that bind to *E. coli*.

8. The method as claimed in claim 7 wherein said screening step comprises (i) labeling said mutants,
(ii) immobilizing *E. coli* in the wells of a microtiter plate,
(iii) adding the labeled mutants to the wells,
(iv) allowing the labeled mutants to bind to the *E. coli*,
(v) washing the wells to remove unbound labeled mutants, and
(vi) identifying the peptide sequences of the bound and labeled mutants.

9. The method as claimed in claim 7 wherein said screening step comprises
(i) immobilizing said mutants within the wells of a microtiter plate,
(ii) adding *E. coli* to the wells,
(iii) allowing the *E. coli* to bind to the immobilized mutants,
(iv) adding to the wells an enzyme-linked antibody against the *E. coli*,
(v) adding a substrate to the wells that exhibits a color change that is catalyzed by said enzyme,
(vi) detecting a color change in the wells to determine the presence of bound mutants therein, and
(vii) identifying the peptide sequences of the bound mutants.

10. The method as claimed in claim 7 wherein said generating step comprises generating a combinatorial library of mutants of said antimicrobial peptide, each of said mutants differing from said antimicrobial peptide by a number of amino acid substitutions.

11. The method as claimed in claim 1 wherein said antimicrobial peptide is selected from the group consisting of SMAP-29, ceratotoxin A, caerulein, PGQ and pleurocidin.

* * * * *